(12) United States Patent
Malinin

(10) Patent No.: US 10,143,562 B2
(45) Date of Patent: Dec. 4, 2018

(54) VERTEBRAL BODY END-PLATE MICROPARTICULATE COMPOSITION AND USES THEREOF

(71) Applicant: Vivex Biomedical, Inc., Marietta, GA (US)

(72) Inventor: Theodore I. Malinin, Key Biscayne, FL (US)

(73) Assignee: Vivex Biomedical, Inc., Atlanta, GA (US)

( * ) Notice: Subject to any disclaimer, the term of this patent is extended or adjusted under 35 U.S.C. 154(b) by 687 days.

(21) Appl. No.: 14/718,796

(22) Filed: May 21, 2015

(65) Prior Publication Data

US 2016/0338844 A1 Nov. 24, 2016

(51) Int. Cl.
*A61F 2/44* (2006.01)
*A61L 27/36* (2006.01)
*A61F 2/30* (2006.01)

(52) U.S. Cl.
CPC .......... *A61F 2/442* (2013.01); *A61L 27/3608* (2013.01); *A61L 27/3658* (2013.01); *A61L 27/3683* (2013.01); *A61F 2002/30754* (2013.01); *A61F 2002/4445* (2013.01); *A61L 2400/06* (2013.01); *A61L 2430/38* (2013.01)

(58) Field of Classification Search
None
See application file for complete search history.

(56) References Cited

U.S. PATENT DOCUMENTS

| 8,318,212 B2 * | 11/2012 | Malinin | A61L 27/3612 424/422 |
| 8,629,122 B2 | 1/2014 | Takahashi et al. | |
| 2003/0069639 A1 | 4/2003 | Sander et al. | |
| 2008/0014179 A1 | 1/2008 | Ferree | |
| 2010/0274362 A1 * | 10/2010 | Yayon | A61K 35/32 623/23.72 |
| 2013/0078222 A1 | 3/2013 | Sakai et al. | |

\* cited by examiner

*Primary Examiner* — Robert A Wax
*Assistant Examiner* — Danah Al-Awadi
(74) *Attorney, Agent, or Firm* — David L. King

(57) ABSTRACT

A particulate composition for stimulating nucleus pulposus regeneration has a particulate composition made of vertebral end-plates having an osseous component wherein the composition is milled, ground or particulized into particles from 10 to 1000 microns in size. At least a part of the composition can be non-demineralized or demineralized or a mixture of demineralized and non-demineralized particles from the vertebral end-plates. Preferably, the non-demineralized part is not subjected to harsh chemical treating. To possibly enhance the release of growth factors and other similar substances from the osseous layer of the end-plate, the material may be treated with hydrochloric acid, ethylene diamine or other demineralizing agents or regimens.

19 Claims, 3 Drawing Sheets

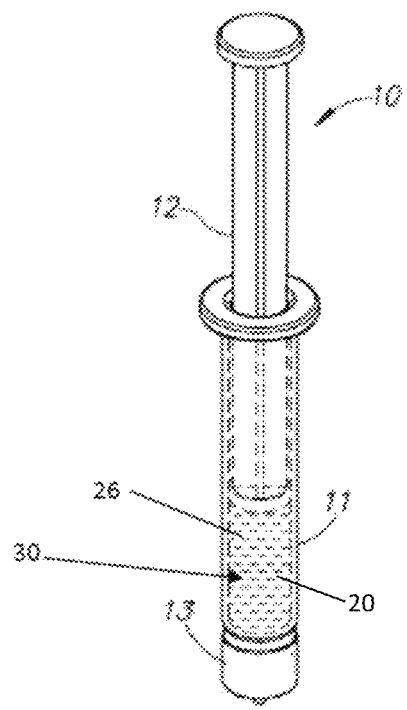
FIG. 4
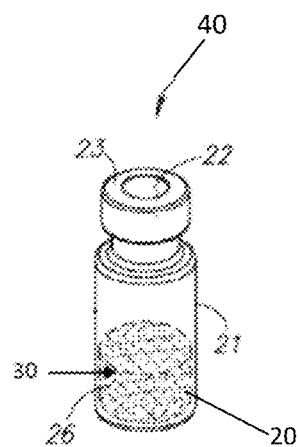
FIG. 5
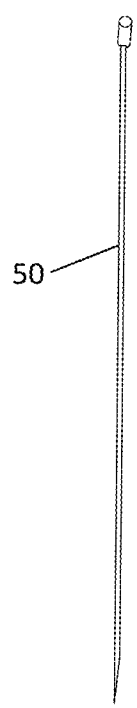

VERTEBRAL BODY END-PLATE MICROPARTICULATE COMPOSITION AND USES THEREOF

FIELD OF THE INVENTION

This application relates to a composition for disc repair and a method for treating diseased discs with the composition.

BACKGROUND OF THE INVENTION

Intervertebral disc degeneration is a common malady which produces low back pain, resulting in disability and in the U.S. health care cost exceeding $100 billion per year. The intervertebral discs are partially movable joints that connect vertebral bodies in the spine. These discs function both to transfer the weight loads and impart mobility. Surgical treatment for symptomatic disc diseases consist of removal of degenerated disc and fusion of the adjacent vertebral bodies, as well as by application of screws, plates and cages. These modalities alter the normal physiology of the vertebral segment. To avoid complications and disadvantages of a spine segment immobilization, regeneration of the intervertebral disc would be preferable. Much effort had been exerted in this direction. Attempts to effect intervertebral disc regeneration included alteration of the phenotype of cells active in the disc, by introducing new cell population, and growth factors, particularly BMP7 and sonic hedgehog (Shh).

Low back pain affects a large number of people. In the U.S. the economic impact exceeds $100 per year. In the majority of patients low back pain is caused by the degenerative changes in the intervertebral disc. The etiology of disc degeneration had not been established with certainty, but its progression is related to aging. Disc degeneration can be viewed as a cascade of events that begins with changes of extracellular microenvironment within the substructure of the disc that progresses with time to anatomic alterations resulting in pathological changes and functional impairment.

As opposed to typical joints of the limbs where mobility is the most important factor and stability is achieved by the supportive soft tissues, the joints of the vertebral column are characterized by stability and resistance to mechanical stress with limited mobility. The connection between the vertebral bodies is unique, as it allows significant degree of movement while withstanding high loads as well as deforming forces.

The intervertebral disc consist of three parts, each made up of different types of connective tissue. The central gelatinous nucleus pulposus is contained by annulus fibrosus which connects the vertebral bodies. Annulus fibrosus is attached to the cartilaginous vertebral end-plate which also contains on osseous component.

The cartilaginous end-plates are integral parts of the intervertebral discs. Although commonly thought of as being made up of hyaline cartilage analogous to that of articular surfaces of joints, in fact, they are quite distinct. Cartilaginous end-plates are not freely articulating, but are blended with coarse collagen strands connecting the cartilage surface with the nucleus pulposus.

In addition, the end-plates give rise to chondrocyte-like cells found throughout nucleus pulposus. The cells are capable of producing and maintaining extracellular matrix as evidenced by the presence of Golgi cisternae and well-developed endoplasmic reticulum. Since some of these cells are necrotic, it follows that these are replaced by new cells originating from the cartilaginous end-plate. Utilization of the biologic properties of this tissue giving rise to these cells constitutes the basis for the present invention.

SUMMARY OF THE INVENTION

The disclosed invention is based on an observation of notochordal cells residing in the nucleus pulposus originating from the cartilage end-plates of the vertebral bodies. The invention consist of micronizing cartilaginous end-plates and introducing this microparticulate composition into diseased intervertebral space to effect intervertebral disc regeneration.

A particulate composition for stimulating nucleus pulposus regeneration has a particulate composition made of vertebral end-plates having an osseous component wherein the composition is milled, ground or particulized into particles from 10 to 1000 microns in size. At least a part of the composition can be non-demineralized or demineralized or a mixture of demineralized and non-demineralized particles from the vertebral end-plates. Preferably, the non-demineralized part is not subjected to harsh chemical treating. To possibly enhance the release of growth factors and other similar substances from the osseous layer of the end-plate, the material may be treated with hydrochloric acid, ethylene diamine or other demineralizing agents or regimens.

The particulate composition for stimulating nucleus pulposus regeneration is preserved by one of freeze-drying, hypothermic dehydration, freezing, chemical desiccation, storage in glycerol, or saline, or balanced salt solution, or petrolatum. The cartilage end-plate can be an allograft or a xenograft material.

In processing, the end-plate tissue is not subjected to any physical treatments that may alter or denature the material of the composition. The end-plate tissue is not subjected to elevated temperatures, temperatures greater than 70° C., that may diminish the stimulating activity of the end-plate tissue. The composition has particles sized between 10 to 1000 microns, preferably between 10 to 500 microns.

A method for stimulating generation of the nucleus pulposus comprises: injecting the particulate composition made of vertebral end-plates having an osseous component wherein the composition is milled, ground or particulized into particles from 10 to 1000 microns in size into a damaged disc.

The step of injecting preferably employs a small bore size cannula to create a small injection hole to permit the damaged disc to close or reseal on withdrawal of the cannula after injection. The method may include the step of mixing the composition in a sterile solution to facilitate flow prior to injection.

The sterile solution is one or more of normal saline; water, lactated ringer's solution; balanced salts; or whole blood;

The method further may have the step of mixing the composition prior to injection with an amount of collagen or other bioabsorbable material to form an injectable paste of relatively high viscosity to allow injection through a cannula while providing a self-sealing of the hole created by the cannula into the damaged disc.

The method further may have the step of withdrawing the cannula from the damaged disc allowing a small portion of injectable paste to at least partially extrude from the hole to close and seal the injection hole in the damaged disc.

BRIEF DESCRIPTION OF THE DRAWINGS

The invention will be described by way of example and with reference to the accompanying drawings in which:

FIG. 4 is a view of a pre-filled syringe with a predetermined amount of the mixture of the cells in a liquid, preferably saline or other suitable liquid.

FIG. 5 is a view of a sealed container or vial containing a mixture of the cells in saline or other suitable liquid or gel.

DETAILED DESCRIPTION OF THE INVENTION

Figure 1:
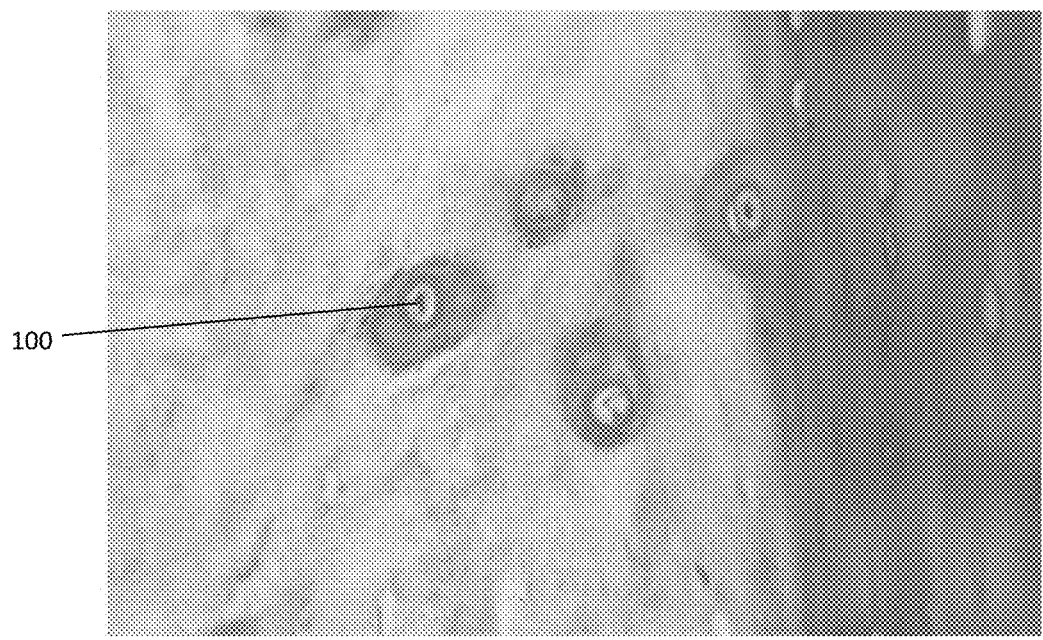
FIG. 1 shows cells which populate normal nucleus pulposus originate from the cartilaginous end-plate. These are sometimes referred to as "notochordal" cells. Photograph shows a cell budding off from a normal end-plate. Two cells have migrated into nucleus pulposus. Periodic acid-Schiff & hematoxylin stain. PAS&H ×900.
Figure 2:
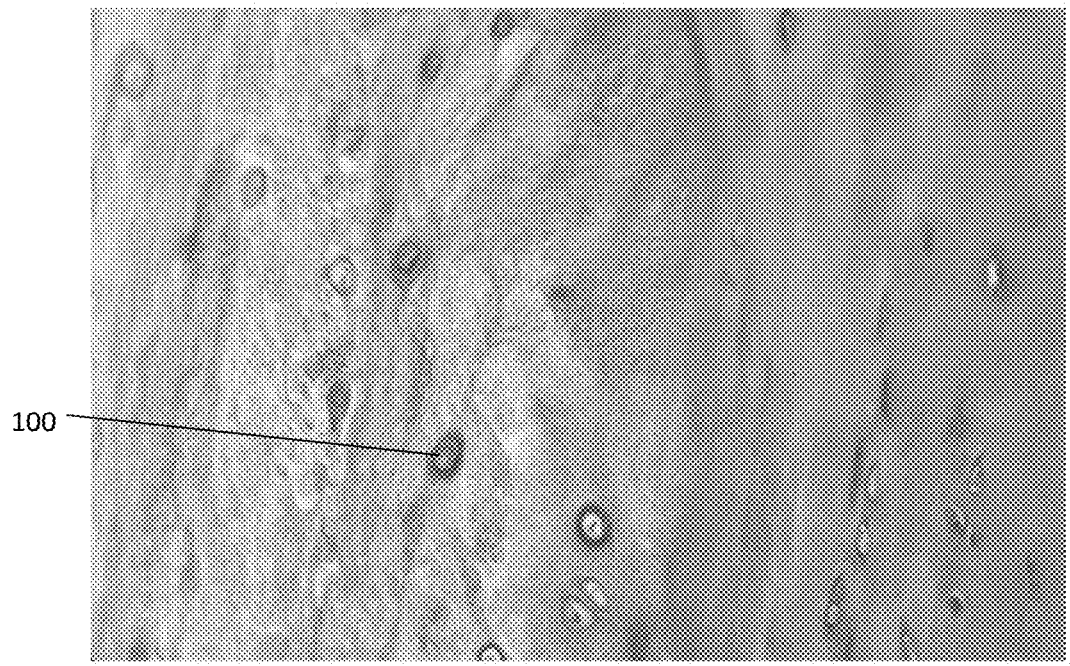
FIG. 2 is a photograph showing cells from the cartilage end-plate migrating into the nucleus pulposus partially dissolved by an enzyme (chondroitinase sulfate), to replace cells damaged by the enzyme. PAS&H ×400.

At the cranial and caudal ends discs abut against cartilaginous end-plate which govern the development of the disc and prevent gelatinous nucleus pulposus from bulging into the vertebral body bone. The end-plates are identifiable from an early embryological stage and have osseous as well as hyaline cartilage components. The cartilage component persists throughout normal maturation and aging while the vertebral bodies undergo ossification. According to the inventor's observation the end-plates generate round notochordal cells found throughout nucleus pulposus. These cells 100 are responsible for maintaining homeostasis of the intervertebral disc, as shown in FIGS. 1 and 2. FIG. 1 shows cells 100 which populate normal nucleus pulposus originate from the cartilaginous end-plate. These are sometimes referred to as "notochordal" cells. FIG. 1 shows a cell budding off from a normal end-plate. Two cells 100 have migrated into nucleus pulposus. Periodic acid-Schiff & hematoxylin stain. PAS&H ×900. FIG. 2 is a photograph showing cells 100 from the cartilage end-plate migrating into the nucleus pulposus partially dissolved by an enzyme (chondroitinase sulfate), to replace cells damaged by the enzyme. PAS&H ×400.

The generation of the cells responsible for the maintenance of the disc and particularly renewal of the nucleus pulposus implies that the cartilaginous end-plate possesses material capable of regenerating the intervertebral disc. Since the end-plate has also an osseous component it is likely also to participate in the maintenance of the intervertebral disc homeostasis. Based on this assumption the invention discloses preparation of particulate vertebral body end-plate composition capable of inducing regeneration of the intervertebral disc.

Nucleus pulposus (NP) cells are essential for the maintenance and the health of the intervertebral disc. Although these cells share some features with articular cartilage (AC) chondrocytes, recent studied have demonstrated clear differences between articular cartilage chondrocytes and NP cells, according to a publication entitled, Arthritis & Rheumatism. 2010, G2 (12) 3695-3705) by Minogue et al.

The above reference authors have identified a number of differentially expressed genes in human NP cells as compared with ACs. This clearly established the differences in phenotypes between NP and AC cells. Thus the novel marker genes of NP cells can be used to characterize and stimulate NP specific differentiation of cells generated by the end-plates of the vertebral bodies. The distinct nature of these cells as well as that of their parent tissue (vertebral body end-plate) constitute the basis for the present invention. Since certain signaling proteins, known to be critical during embryonic development, continue to be expressed in post-natal nucleus pulposus, stimulation of the production of these proteins, as well as that of the NP cells will be provided by the micronized vertebral end-plate tissue composition.

Figure 3A:
FIG. 3A shows a vertebral end-plate exhibiting its cartilaginous component (blue) and osseous component (red) from an animal (baboon) whose intervertebral disc was injected with 10 µ/ml of chondroitinase sulfate. Masson's trichrome stain ×100.
Figure 3B:
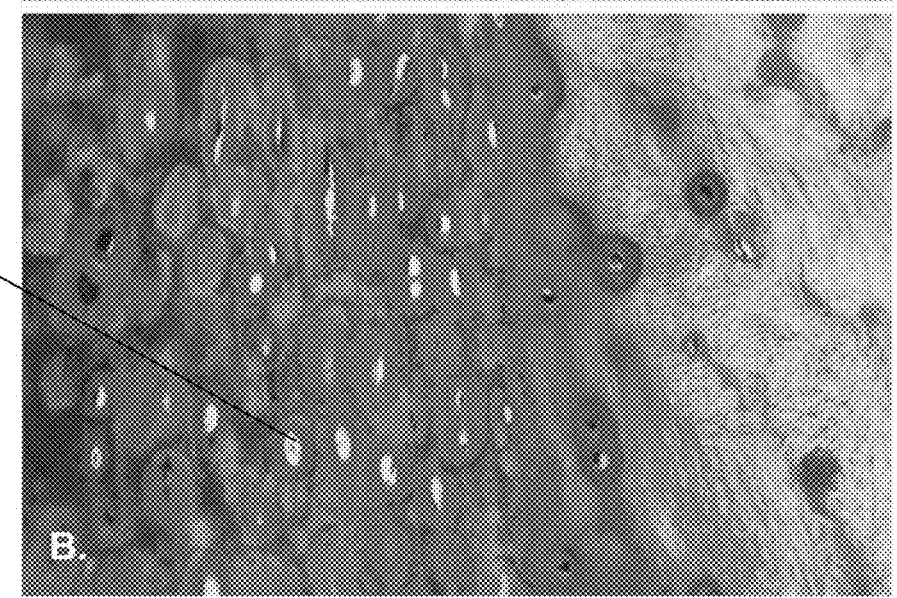
FIG. 3B shows a higher magnification of the vertebral body end-plate illustrating the cartilage layer generating nucleus pulposus cells ×400.

In accordance with the present invention particulate composition of the vertebral end-plates for stimulating nucleus pulposus regeneration comprises non-demineralized composition. Since vertebral body end-plates also incorporate osseous component, as shown in FIGS. 3A and 3B. FIG. 3A shows a vertebral end-plate exhibiting its cartilaginous component (blue) and osseous component (red) from an animal (baboon) whose intervertebral disc was injected with 10 µ/ml of chondroitinase sulfate. Masson's trichrome stain ×100. FIG. 3B shows a higher magnification of the vertebral body end-plate illustrating the cartilage layer generating nucleus pulposus cells ×400. These can also be demineralized to facilitate release of stimulating substances. Cells 100 found within nucleus pulposus are not the same as chondrocytes from articular cartilage. Their phenotype is different from articular cartilage phenotype. Therefore, cartilaginous end-plate which produces nucleus pulposus cells 100 when compared to NP cells 100 derived from the normal nucleus pulposus, as shown in FIGS. 1 and 2, is a specialized structure.

The cartilage end-plate with its osseous component can be separated from the vertebral body, with a sharp instrument, down to the trabecular bone of the vertebra. From the vertebral body, the end-plate cartilage for use in the present invention may include osseous component of the end-plate. It may comprise allogeneic and/or xenogeneic tissue.

The end-plate cartilage with its osseous component can be non-demineralized or demineralized. Preferably, non-demineralized cartilage is not subjected to harsh chemical treatments which can alter the inherent natural properties of the material. On the other hand, to possibly enhance the release of growth factors and other similar substances from the osseous layer of the end-plate, the material may be treated with hydrochloric acid, ethylene diamine or other demineralizing agents or regimens. In some embodiments non-demineralized or demineralized particulate end-plate may be subjected to microbiologic testing or other testing methods that do not deleteriously alter the material.

Additionally, the end-plate tissue is not subjected to any physical treatments that may alter or denature the material of the composition. For example, end-plate tissue is not subjected to elevated temperatures, e.g. temperatures greater than 70° C. that may diminish the stimulating activity of the end-plate tissue. However, end-plate material may be preserved by freezing, cryopreservation, freeze-drying, hypothermia desiccation or chemical dehydration. Two preferred methods of preserving end-plate tissue are: intact, micronized, pulverization, or in other physical configuration, by hypothermic dehydration or by freeze-drying.

The composition includes non-demineralized or demineralized or combinations thereof of end-plate particles preferably having a distribution of particle sizes from 10-1000 microns. The particles may have particle sizes distributed within the range from about 10 to about 800 microns; more preferably distributed in the range of 70 to 300 microns. Some composition according to the present invention, may include particles having sizes greater than 70 microns in the form of vertebral end-plate granules. In some embodiments, the composition may comprise a combination of vertebral end-plate powder and vertebral end-plate granules, the powder being below 70 microns and the granules greater than 70 microns in size.

Vertebral end-plate composition, according to the present invention may be produced by grinding or cryo-milling non-demineralized vertebral body end-plate to produce particle sizes of desired dimensions. The end-plate tissue may be in the form of dry tissue, freeze-dried tissue, hypothermically desiccated tissue, frozen tissue, wet tissue or mixtures thereof. A particular tissue composition of desired dimensions can be decalcified by immersion into INhydrochloric acid or other decalcifying agents. For example, pieces of tissue obtained from the vertebral body end-plates, superior or inferior, are washed in several changes of normal saline, lactated Ringer's solution, phosphate buffered saline or any other balanced salt solution, or tissue culture medium. The tissue is blotted dry and frozen rapidly (at about 10° C./minute or faster) in the vapor phase of liquid nitrogen or a mechanical freezer with chamber temperatures below −100° C. Alternatively, the tissue may be frozen directly in liquid nitrogen (about −196° C.). Frozen tissue is preferably rapidly placed on a pre-cooled shelf of a freeze-drying apparatus. The shelf is preferably maintained at about −40 to −50° C. or below. The freeze-dryer condenser is maintained at about −70° C. or lower. A vacuum level of less than 100 mTorr is preferably maintained in the freeze-dryer chamber during the freeze-drying cycle. Following freeze-drying the moisture content of the tissue is reduced to about 5%. Over-drying below 5% results in cracking of the tissue and denaturing of protein.

It is well known in the art that freeze-drying results in certain undesirable side effects. Most of these are related to freezing and distortion of tissues by ice-crystal formation. To avoid these undesirable side effects of freeze-drying an alternate method of tissue preservation preferably uses dehydration at hypothermia, as recommended as a best practice by the inventor. The method consists of placing tissue at hypothermic temperatures (2 to 15° C.) in a vacuum chamber. The process results in a dried tissue without undesirable alterations caused by freezing.

The non-demineralized vertebral end-plate tissue may be ground using any suitable grinding apparatus. For example, any grinding apparatuses such as cryo-mills, which can grind hard, brittle material in seconds, can be employed for this purpose. Grinding must be performed without heating the material above 70° C., a temperature above which BMPs are deactivated.

After each grinding cycle the tissue particles are sieved through a sieve of 70 to 500 microns. Sieving can also be used to separate powder from the granular material.

The present invention also provides a method for stimulating regeneration of the nucleus pulposus without relying on any cells directly from the nucleus pulposus material, but rather from the uniquely structured cells or cell fragments of the adjacent end-plates. Therapeutically effective amounts of particulate vertebral end-plate tissue comprising non-demineralized or demineralized tissue composition or combinations thereof having particle size distributed within the range of 10 to 800 microns, preferably 10 to 500, may be administered into damaged intervertebral discs by means of injection, preferably via a cannula of sufficiently small size to allow the injection hole to close or reseal. To facilitate the flow of the composition, it can be mixed in a sterile solution of one or more of: normal saline; water, lactated ringer's solution; balanced salts; or whole blood; alternatively, the composition can be mixed with an amount of collagen or other bioabsorbable material prior to injection to form an injectable paste of relatively high viscosity to allow injection through a cannula while providing a self-sealing of the hole created on penetration of the cannula into the damaged disc, a small portion of the paste being allowed to extrude from the hole to close and seal the injection hole created in the damaged disc.

As shown in FIGS. 4 and 5, the fluid or paste mixture 30 with the particulate composition 20 is shown is a pre-filled syringe 10 and a sealed container or vial 40, respectively. The fluid or paste mixture 30 has the particulate composition 20 dispersed uniformly in a carrier medium or liquid 26. In either delivery system, the mixture 30 can also be filled with saline or other suitable liquid or gel to facilitate a repair or treatment dosage.

As shown in FIG. 4, the syringe 10 has a plunger 12 sealed inside the housing 11 closed by a removable cap 13. The syringe 10 can also have a cannula or needle 50. The plunger 12 withdrawn to provide volumetric space for the pre-filled mixture 30. Once the cap 13 is removed, a nozzle is exposed to deliver the mixture 30 to the target area to be treated through the cannula or needle 50.

Alternatively, as shown in FIG. 5, the entire fluid or paste mixture 30 can be provided in a sealed vial or container 40. An end cap 23 encircles an injectable elastomeric stopper 22 at one end or top of a housing 21. The particulate composition 20 is inside the container housing In another embodiment, a sterile cartilage end-plate implant material made as the particulate composition 20 intended for intervertebral disc repair, the particulate ranging from 10 to 1000 microns in size can be dispersed in a bioabsorbable carrier including gelatin, collagen, chitosan, alginate, buffered saline, balanced salt solutions, polymers, dextran, sodium hyaluronate, and hyaluronic acid and its derivatives, as well as polyvinylpyrrolidinone, hydroxyethyl starch and collodion. In another embodiment, autologous or allogeneic stem cells can be added to the bioabsorbable carrier or carrier with end-plate microparticulate composition 20.

Without wishing to be bound to any theory, it is believed that composition, according to the present invention, including non-demineralized and/or demineralized particulate vertebral end-plate tissue will release growth factors or other substances that will induce regeneration of the intervertebral discs.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:
1. A particulate composition for stimulating nucleus pulposus regeneration comprising:
    a particulate composition made of cartilaginous end-plates taken from vertebral end-plates having an osseous component or layer wherein the composition is milled or ground into particles from 10 to 1000 microns in size, wherein the cartilaginous end-plates taken from the vertebral end plates include a blend of coarse collagen strands and material for budding notochordal cells.

2. A particulate composition for stimulating nucleus pulposus regeneration comprising:
a particulate composition made of cartilaginous end-plates taken from vertebral end-plates having an osseous component or layer wherein the composition is milled or ground into particles from 10 to 1000 microns in size, wherein the cartilaginous end-plates taken from the vertebral end plates include a blend of coarse collagen strands and material for budding notochordal cells, wherein at least a part of the composition is non-demineralized.

3. The particulate composition for stimulating nucleus pulposus regeneration of claim 1 wherein at least a part of the composition is demineralized.

4. The particulate composition for stimulating nucleus pulposus regeneration of claim 1 wherein the composition is a mixture of demineralized and non-demineralized particles from the vertebral end-plates.

5. The particulate composition for stimulating nucleus pulposus regeneration of claim 1 wherein the composition is preserved by one of freeze-drying, hypothermic dehydration, freezing, chemical classification, storage in glycerol, or saline, or balanced salt solution, or petrolatum.

6. The particulate composition for stimulating nucleus pulposus regeneration of claim 1 wherein the vertebral end-plate is an allograft or a xenograft material.

7. The particulate composition for stimulating nucleus pulposus regeneration of claim 2 wherein the non-demineralized part is not subjected to harsh chemical treating.

8. The particulate composition for stimulating nucleus pulposus regeneration of claim 2 wherein the vertebral end plates are treated with one of hydrochloric acid, ethylene diamine or other demineralizing agents or regimens to enhance a release of growth factors and other similar substances from the osseous component or layer of the vertebral end-plates.

9. The particulate composition for stimulating nucleus pulposus regeneration of claim 1 wherein the end-plate tissue is not subjected to any physical treatments that may alter or denature the material of the composition.

10. The particulate composition for stimulating nucleus pulposus regeneration of claim 9 wherein the end-plate tissue is not subjected to temperatures greater than 70° C., that may diminish the stimulating activity of the end-plate tissue.

11. The particulate composition for stimulating nucleus pulposus regeneration of claim 1 wherein the composition has particles sized between 10 to 800 microns.

12. The particulate composition for stimulating nucleus pulposus regeneration of claim 11 wherein the composition has particles sized between 10 to 500 microns.

13. The particulate composition for stimulating nucleus pulposus regeneration of claim 12 wherein the composition has particles sized between 70 to 300 microns.

14. A method for stimulating generation of the nucleus pulposus comprising:
injecting the particulate composition of claim 1 wherein the composition is milled, ground or particulized into particles from 10 to 1000 microns in size into a damaged disc.

15. The method of claim 14 wherein the step of injecting employs a small bore size cannula to create a small injection hole to permit the damaged disc to close or reseal on withdrawal of the cannula after injection.

16. The method of claim 15 further comprises the step of:
mixing the composition in a sterile solution to facilitate flow prior to injection.

17. The method of claim 16 wherein the sterile solution is one or more of normal saline; water, lactated ringer's solution; balanced salts; or whole blood.

18. The method of claim 14 further comprises the step of:
mixing the composition prior to injection with an amount of collagen or other bioabsorbable material to form an injectable paste of relatively high viscosity to allow injection through a cannula while providing a self-sealing of the hole created by the cannula into the damaged disc.

19. The method of claim 18 further comprises the step of:
withdrawing the cannula from the damaged disc allowing a small portion of injectable paste to at least partially extrude from the hole to close and seal the injection hole in the damaged disc.

* * * * *